United States Patent [19]

Reeves et al.

[11] 3,958,177

[45] May 18, 1976

[54] PARTICLE ANALYZING DEVICE WITH CHANGEABLE APERTURE MEANS

[75] Inventors: Richard A. Reeves, Creve Coeur; James F. LaHay, St. Louis, both of Mo.

[73] Assignee: Sherwood Medical Industries Inc., St. Louis, Mo.

[22] Filed: Dec. 17, 1974

[21] Appl. No.: 533,584

[52] U.S. Cl. ............... 324/71 CP; 73/432 PS
[51] Int. Cl.² ............... G01B 27/02; G01R 27/00
[58] Field of Search ............ 324/71 CP; 73/432 PS, 73/28, 61 R; 210/387

[56] References Cited
UNITED STATES PATENTS

| | | | |
|---|---|---|---|
| 3,475,965 | 11/1969 | Koblin et al. | 73/28 |
| 3,485,086 | 12/1969 | Roman | 73/61 R |
| 3,614,607 | 10/1971 | Schoen | 324/71 CP |
| 3,672,507 | 6/1972 | Paull, Jr. | 210/387 |
| 3,815,024 | 6/1974 | Bean et al. | 324/71 CP |

*Primary Examiner*—John K. Corbin
*Assistant Examiner*—Wm. H. Punter
*Attorney, Agent, or Firm*—Stanley N. Garber; William R. O'Meara

[57] ABSTRACT

A particle analyzing device in which a suspension of particles in a fluid medium is passed through an aperture in a strip of plastic material, and the change in the conductivity of the suspension across the aperture, each time a particle flows through the aperture, is detected so that the number and volume of particles for a given quantity of the suspension can be determined. The strip can be provided with a plurality of scanning apertures and be selectively moved across the flow path to bring a new aperture into an operative position in the flow path, such as when an aperture becomes clogged by debris.

15 Claims, 5 Drawing Figures

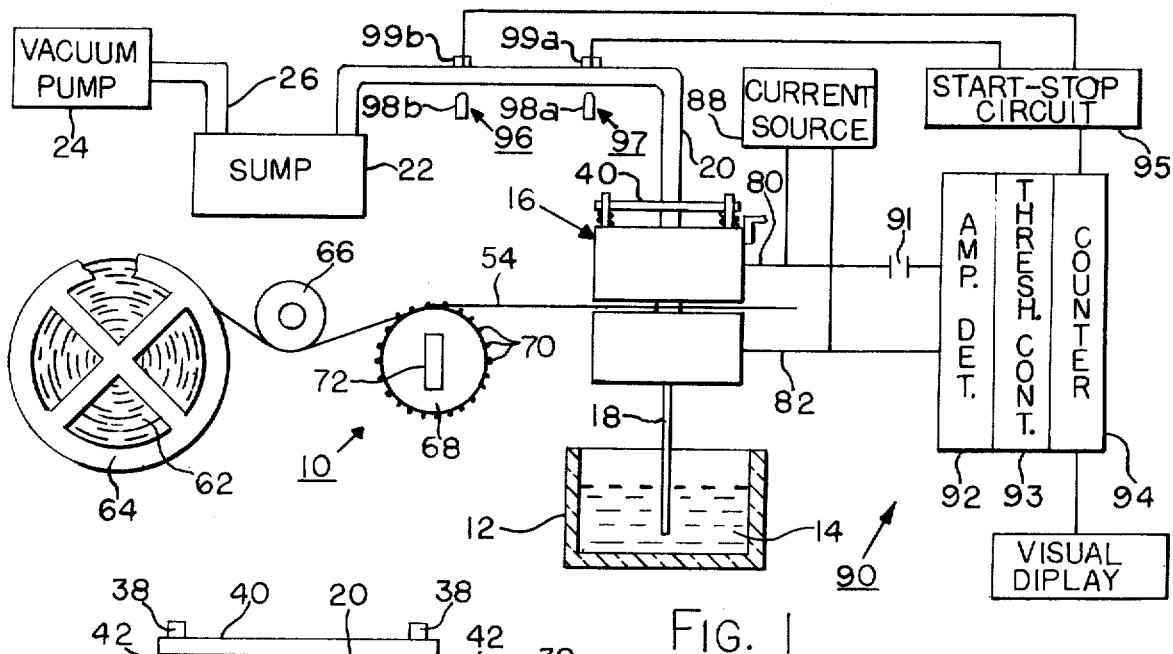
FIG. 1
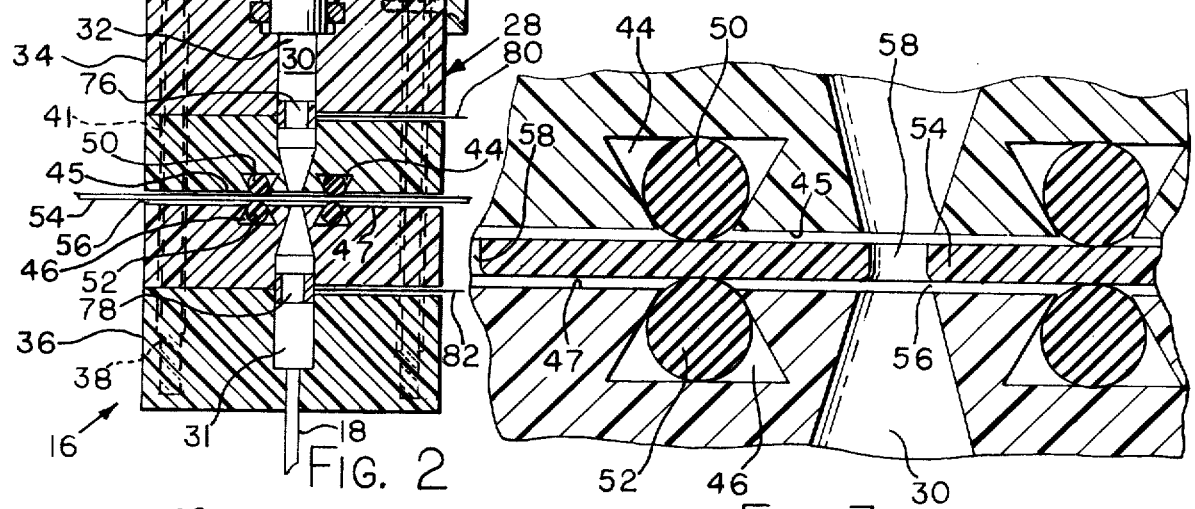
FIG. 2
FIG. 3
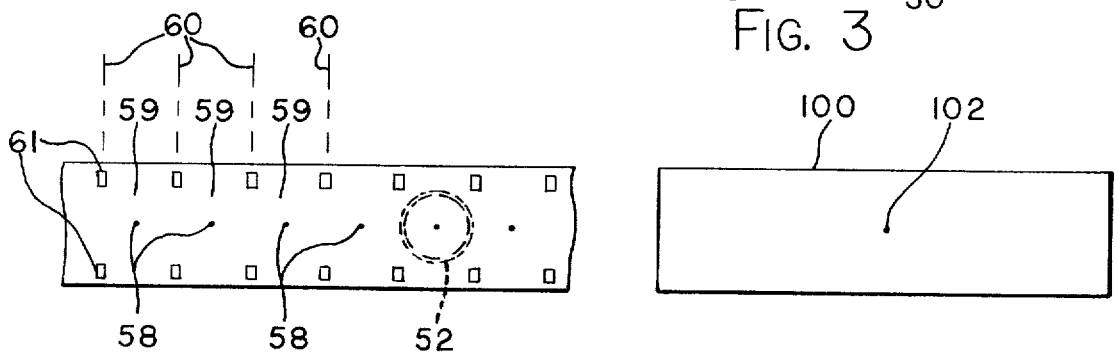
FIG. 4
FIG. 5

PARTICLE ANALYZING DEVICE WITH CHANGEABLE APERTURE MEANS

BACKGROUND OF THE INVENTION

This invention relates to particle analyzing devices and more particularly to analyzing devices in which a suspension of particles in a fluid medium is passed through an aperture and the change in impedance of the suspension material when a particle moves through the aperture is detected.

In the Coulter patent, U.S. Pat. No. 2,656,508, a small aperture is provided in a vessel, such as a test tube, and the tube is inserted into another vessel, such as a glass beaker containing a suspension of particles in a fluid medium. Electrodes are disposed in the suspension on opposite sides of the aperture and connected to a current source. Suspension is moved between the vessels through the aperture. As each particle passes through the aperture, it effects a change in the impedance of the suspension between the electrodes to produce a signal or current pulse. When counting blood cells, the suspension is a mixture of blood and a liquid such as a saline solution, in a known ratio, so that by counting the number of signals for a known volume of suspension passing through the aperture, the number of cells for a given quantity of blood is readily ascertainable. The magnitude of the signal determines the size of the particle so that not only can the number of particles be determined but the size or mean size of particle per volume of suspension can be determined. As is well known, such particle analyzing systems are especially useful in determining the number of red and white blood cells per unit volume of blood and the mean cell volume.

Where the particles are small, such as in the case of blood cells, the scanning aperture must, of course, also be small so that a particle moving through the aperture will cause a significant or detectable change in impedance of the suspension across the aperture. Because of the small aperture, foreign particles or debris sometimes present in the fluid medium, such as dust and lint, may cause blockage of the aperture. This clogging of an aperture results in an invalid determination of the number or the size of the particles, as well as a loss of time when an analysis must be repeated. Where the aperture is provided in the wall of a test tube or the like, the tube is disposed in a filled container or beaker, and it is necessary to stop the counting or other analysis and brush or otherwise open the aperture such as by back-flushing the suspension through the aperture. The cleaning problem is further compounded when current densities result in "cooking" the debris onto the aperture side walls. In U.S. Pat. No. 3,395,344, at attempt to overcome the problem of clogged apertures is made by providing a flexible diaphragm with an aperture formed therein which is intended to distort due to increased fluid pressure as debris accumulates at the aperture so as to eventually enlarge the aperture sufficiently to pass the blockage. This is not an entirely satisfactory solution to the problem of clogging since at times there is partial clogging which may vary the effective size of the aperture over an extended period of time before enough debris has accumulated to adequately enlarge the aperture. Also, the aperture varies in size because the diaphragm stretches. Since the effective size of the aperture is generally critical to an accurate analysis, the results from such an apparatus may not always be accurate. In U.S. Pat. No. 3,783,376, a particle scanning or counting cell arrangement is provided by placing a jewel with the aperture therein, in a hole formed in a thin plastic slide member and inserting the slide member between opposed o-rings in the flow path of a receptacle so that the suspension flows through the aperture in the jewel. In this way, the slide may be removed from the scanning cell by sliding it out of the receptacle to remove lodged particles in the aperture. In can also be flicked or vibrated to remove the particles causing the blockage of the aperture while in the receptacle. However, with such a construction, flicking the slide may cause the clogging material to return to the upstream side of the aperture and subsequently clog the aperture or the aperture may only be partially opened by the flicking action. In the above-mentioned devices, it is necessary, in order to be sure that the aperture is completely open, to view the aperture with a microscope.

SUMMARY OF THE INVENTION

Accordingly, it is an object of the present invention to provide an improved particulate analyzing device in which the above disadvantages are substantially overcome.

Another object of the present invention is to provide an improved device for analyzing particulate matter suspended in a fluid medium in which the particles pass through an aperture wherein the device can be economically used without the necessity of unblocking the aperture should it become clogged, and wherein the use of a microscope for checking the aperture is obviated.

Still another object is to provide a device for analyzing particulate matter suspended in a liquid medium, such as for blood cell counting, wherein the changing from one scanning aperture to another is economically, easily and quickly made.

In accordance with one aspect of the present invention, a particle analyzing device is provided which includes a passageway for the flow of suspension, a strip having a plurality of scanning apertures spaced lengthwise of the strip, the strip being movable from a position in which one of the apertures is in an operative position in the passageway to another position in which a second aperture is disposed in an operative position in the passageway. In accordance with another aspect of the invention, a plastic scanning element is provided with a scanning aperture having walls which are integral portions of the element.

These, as well as other features and advantages of the present invention will become apparent from the following description and accompanying drawings.

BRIEF DESCRIPTION OF THE DRAWINGS

FIG. 1 is a diagramatic view of blood cell counting apparatus in accordance with a preferred embodiment of the present invention;

FIG. 2 is an enlarged vertical section of the particulate suspension analyzing sensor of FIG. 1;

FIG. 3 is a greatly enlarged fragmentary view of the sensor shown in FIG. 2;

FIG. 4 is a fragmentary plan view of apertured strip material used in the apparatus of FIG. 1; and FIG. 5 is a plan view of apertured strip material of modified construction.

DESCRIPTION OF THE PREFERRED EMBODIMENT

Referring now to the drawings and particularly to FIG. 1, a diagramatic illustration of a particle analyzing device is indicated at 10. While the device 10 can be employed to study or analyze various types of particulate suspensions, it will be described herein as a blood cell counting device.

A receptacle or beaker 12 is shown containing a suspension sample 14 which is a mixture of blood and a diluent or electrolyte in a known ratio. The diluent may be a saline solution which, of course, has a higher conductivity per unit volume than the particle or blood cell which is to be counted.

In the illustrated embodiment, the blood cell counting apparatus 10 includes a particle scanning or counting device or sensor 16 that is connected in fluid communication with the sample 14 by means of an inlet conduit 18. The liquid suspension 14 is drawn through the counting chamber 16 and an outlet conduit 20 to a container or sump bottle 22 connected to the outlet conduit. A vacuum pump 24 is connected by a conduit 26 to the sump bottle to provide a negative pressure or suction in bottle 22 for drawing the suspension from container 12.

As seen in FIG. 2, the counting sensor 16 includes a housing 28 having a fluid passageway 30 extending therethrough and having an inlet 31 at the lower end connected to conduit 18, and an outlet 32 at the upper end connected to the conduit 20. The housing includes relatively movable upper and lower housing portions or block members 34 and 36 connected together by four corner posts 38. The upper housing member 34 is shown connected to a standard or stationary member 39. The posts 38 are slidable in holes 41 in the upper member 34 and are threadedly connected at their lower ends to the lower housing member 36. Each pair of adjacent posts are shown for illustration as connected together by a horizontal bar 40. A coil spring 42 is compressed between each bar 40 and the upper side of housing member 34. The lower housing member 36 is normally urged upwardly toward engagement with the upper block 34 by the springs 42. Posts 38, in response to a downward force applied to the bar 40, move the lower housing block 36 away from upper housing member 34. An annular groove 44 is formed in the bottom wall 45 of housing member 34 and an annular groove 46 is formed in the upper wall 47 of housing member 36 in axially aligned relation with groove 44, as also seen in FIG. 3. A pair of opposed sealing elements, shown as o-rings 50 and 52, are respectively disposed in the annular grooves 44 and 46 in facing axial alignment with each other.

An apertured scanning member in the form of a strip 54 extends through a horizontal opening 56 in the housing 28 and extends between the o-rings 50 and 52, the strip intersecting the passageway 30. The opening 56 is formed by the space between the facing walls 45 and 47 of the housing members 34 and 36 in the illustrated embodiment.

The strip 54 is provided with a plurality of scanning apertures 58 predeterminately spaced along the length of the strip. As seen in FIG. 4, the strip 54 includes a plurality of like integral scanning elements 59, each defined, for example, by a portion of the strip between adjacent broken lines 60, with each element having one of the apertures 58 at its center. The strip is a unitary or single-piece member and, as seen in FIG. 3, the side walls of each scanning aperture 58 are integral portions of the strip and, of course, are of the same material as the strip. Apertures 58 are adapted to be positioned selectively, one at a time, in an operative position in the passgeway 30, as will be explained in greater detail hereafter.

The strip 54 is of insulating material, such as a suitable synthetic plastic material, such as polyester film. A preferred material is a film of ethylene glycol terephthalate (Mylar film). A preferred form of strip material is conventional motion picture film leader, such as transparent 16 millimeter (Mylar film) leader having sprocket holes 61 along the opposed margins and provided with apertures 58. While the material of strip 54 is preferably flexible so that it can be wound upon itself into a supply roll 62, it is preferable substantially nonelastic or stretchable so that the size of the scanning aperture remains fixed for accurate test results under usual operating conditions and even if the aperture becomes clogged. As seen in FIG. 1, a supply roll 62 of the strip 54 is mounted for rotation on a mandrel or reel 64 with the strip fed around a tensioning roller 66 and over a rotatable sprocket 68 having two peripheral rows of sprocket teeth 70 which enter the holes 61 and advance the strip through the housing opening 56 in response to rotation of the sprocket. A handle 72 is shown on the drive sprocket 68 for manually rotating the sprocket to advance the strip. However, other means, such as a lever may be coupled to the shaft of sprocket 68 and to the horizontal bars 40 (FIG. 2) and arranged to move the housing members 34 and 36 apart and then index or rotate the sprocket 68 a predetermined amount to selectively advance the strip 54 to move a selected aperture or scanning element 59 into an operative position in the housing passageway 30 within the sealing rings 50 and 52.

In FIG. 3, the scanning strip 54 is shown extending between the o-rings 50 and 52 and with an aperture 58 in an operative position in the passageway 30. Each of the o-rings is shown having an inner diameter which is less than the distance between adjacent or successive apertures 58 so that the o-rings sealingly engage the opposite sides of the strip with only one aperture operatively disposed radially inwardly of the o-rings and in the liquid flow path of passageway 30. As seen in FIG. 4, the apertures are along the lengthwise center line of the strip and are equidistant from the four adjacent sprocket holes 61. The o-ring 52 is shown in phantom in FIG. 4 as having an outer diameter less than the distance between the inner edges of opposed sprocket holes 61 at the opposite sides of the strip so as to seal only one aperture 58 in the passageway 30.

A pair of electrodes 76 and 78 are disposed in passageway 30 on opposite sides of the strip 54 with the particle scanning chamber portion of the passageway between the electrodes. The electrodes are shown as cylindrical metal sleeves, for example, of stainless steel, frictionally secured in position respectively in the housing members 34 and 36. In the illustrated embodiment, the housing 28 is formed of insulating material such as molded, clear acrylic plastic so that the walls of the scanning chamber are nonconductive and the suspension can be seen as it flows through the scanning chamber and passageway 30. Each of the housing members 34 and 36 is shown formed of a pair of blocks which are fixed together such as by a suitable cement with mating surfaces grooved to provide a convenient exit for a pair of conductive leads 80 and 82 respectively connected to the electrodes 76 and 78 and which extend to the exterior of the housing for connection with electrical control and detection circuits to be described.

In the case of blood cell counting apparatus, each aperture 58 may be between about 75 and 100 microns in diameter and the effective length of the scanning aperture about ¾ of the diameter. The apertures 58 are preferably formed by burning holes through the strip by means of a laser beam and in such case, one side of the aperture is somewhat conical so that the effective length of the aperture is slightly less than the thickness of the strip material. Using a laser beam, a strip of material having a thickness of 100 microns was provided with apertures having an effective length of about 75 microns and a diameter of about 100 microns.

Electronic control and counting circuits are shown in simple block diagram form and may be of any suitable or conventional design. For example, the electrical systems disclosed in U.S. Pat. Nos. 3,259,842 and 3,473,010 may be used in analyzing suspension liquid 14 flowing through the scanning sensor 16. In the blood cell counting system 10 of FIG. 1, for example, a constant current source, such as indicated at 88, is connected to the electrodes 76 and 78 by leads 80 and 82, and an electronic detecting system, indicated generally at 90, is connected to the leads through an isolating capacitor 91. The electronic detecting system 90 may include a voltage detector and amplifier 92 for receiving a voltage pulse across the electrodes each time a cell flows through the scanning aperture 58. System 90 also is shown including a variable threshold control and pulse shaping circuit 93 wich may be used to suppress extraneous variations or "noise" in the signals from the amplifier so that the signals or pulses are suitable for use in an electronic counter circuit 94. The counter circuit may be started and stopped in response to a start-stop circuit 95 which receives start-stop signals, for example, from a pair of photosensitive devices indicated at 96 and 97. These photosensitive devices includes light sources 98a and 98b and light sensitive cell 99a and 99b and are responsive to the leading edge of the column of suspension liquid flowing in tube 20. In this way, a known quantity of suspension, as determined by the volume of the tube between the devices 96 and 97, can be passed through the scanning aperture 58 for a given test cycle. A visual display device, such as a meter or other numerical read-out or indicating device, can be correlated with the number of signal pulses produced for the given quantity of suspension analyzed to produce a visual indication of the number of cells per unit volume of blood. By properly varying the threshold level, signals from the electrodes 76 and 78 can be used to count red, as well as white blood cells. Instead of varying the threshold, two differently sized scanning apertures could be used, one for red cell counting and the other for white cell counting.

Whenever foreign particles clog the aperture 58 in the sensor 16, or if such an occurrence is suspected, such as by obtaining a subnormal blood cell count, a new aperture 58 can be quickly and easily substituted for the one in the scanning sensor. Where the housing 28 is formed of two separable members as shown, the suspension chamber or passageway may be removed from the scanning chamber or passageway 30, the housing members separated, the sprocket wheel 68 rotated to advance the strip 54 a predetermined distance to position the next successive new aperture 58 in an operative position in the flow path or passageway 30, and the housing members allowed to return to the closed condition shown in the drawing. If desired, the sprocket 68 may be disposed on the right side of the scanning sensor 16 to pull the strip 54 through the sensor, and, in some cases, while the o-rings are resiliently engaged with the opposite sides of the strip.

Thus, instead of dislodging debris from a clogged or partially clogged scanning aperture, it is a simple matter to replace one aperture with a new one in the device of the present invention. By eliminating the necessity of unclogging an aperture, there is a savings in time and labor, and when a new aperture is moved into the operative position, there is an assurance that a clear aperture is present in the system. Because of the economical nature of the apertured plastic strip 54, and the ease with which apertures can be changed, apertures can be replaced often, and the necessity of a microscope to check an aperture for clogging is avoided. Also, the scanning strip 54 may be automatically advanced to position a new scanning element and aperture in an operative position in the sensor 16 at the end of each test cycle, for example, by an automatically controlled solenoid or motor, if desired.

While it is possible to advantageously use separate plastic scanning elements, it will be apparent that a relatively large number of scanning elements 59 are conveniently held and stored together by forming them integrally with each other in a unitary plastic strip, and especially where the strip can be wound into a supply roll as at 62 in the drawing.

In FIG. 5, a modified form of scanning element, which is indicated at 100, is in the form of a strip of plastic material having a single scanning aperture 102, although it could be provided, in some cases, with more than one aperture. In this construction, a plurality of such scanning elements can be readily selectively inserted, one at a time, into a sensor, such as the sensor 16. The material and the width and thickness of the strip 100, and the aperture dimensions may be the same as those for the strip 54 of FIG. 4.

While a preferred form of the invention has been described herein, it will be apparent that various changes and modifications thereto may be made without departing from the spirit of the invention or scope of the invention as defined in the appended claims.

What is claimed is:

1. A device for analyzing a fluid suspension including particles and a fluid medium having a conductivity per unit volume different from that of the particles comprising fluid passageway means for passing fluid suspension therethrough for analysis, a plurality of scanning elements of plastic insulating material integrally connected together in successive order to form a unitary strip of plastic material, each of said elements having a scanning aperture therethrough with the side walls of each of said apertures being integral portions of said strip and with said apertures spaced lengthwise of said strip, said strip being formed of a material which is sufficiently flexible as to be capable of being wound upon itself into a supply roll or other configuration, means for supporting said strip for movement to selectively feed said elements, one at a time, into an operative position in said passageway means wherein suspension can flow through the aperture of the operatively positioned element, each of said apertures being sized so that a detectable change in the conductivity of the suspension occurs in an operatively positioned aperture when a particle passes therethrough, and means for detecting a change in the conductivity of the suspension in the aperture of the operatively positioned element when a particle passes therethrough.

2. The device of claim 1 wherein said strip comprises a flexible plastic film which includes ethylene glycol terephthalate.

3. The device of claim 1 wherein only one of said apertures at a time is within the flow path of the suspension.

4. The device of claim 1 wherein said strip includes a portion thereof wound upon itself to define a supply roll of scanning elements.

5. The device of claim 4 wherein said strip has sprocket holes therein, and the device further includes a sprocket wheel member cooperable with said sprocket holes for moving said strip.

6. A blood cell analyzing device comprising a passageway for the flow therethrough of a sample suspension including blood cells and a liquid medium having a conductivity per unit volume higher than that of the cells, a strip of insulating plastic material having a plurality of scanning apertures therein spaced lengthwise of said strip, the side walls of each of said scanning apertures being integral portions of said strip of plastic material, said strip being movable across said passageway to selectively position said apertures, one at a time, in an operative position in said passageway wherein suspension can flow through the operatively positioned aperture, said strip being formed of a material which is sufficiently flexible as to be capable of being wound upon itself into a supply roll or other configuration, electrode means disposed for contact with the suspension on each of the opposite sides of said strip, each of said apertures being sized so that a detectable change in conductivity of the suspension between said electrode means occurs when a blood cell passes through an operatively positioned aperture, circuit means coupled to said electrode means for producing signals in response to changes in the conductivity of the suspension between said electrode means, and means for detecting said signals.

7. The device of claim 6 wherein said strip of insulating material includes a portion thereof wound upon itself to form a supply roll thereof.

8. The device of claim 6 wherein said electrode means comprise a pair of electrodes disposed in said passageway on opposite sides of said strip.

9. The device of claim 6 including a housing through which said passageway extends having an opening intersecting said passageway, said strip being movable through said housing opening for movement across said passageway.

10. The device of claim 9 wherein said strip of material includes a supply roll of said material, said device further including means for feeding said strip of material from said supply roll through said housing opening to selectively position successive apertures in an operative position in said passageway.

11. The cell device of claim 10 wherein said strip material is ethylene glycol terephthalate.

12. The device of claim 10 wherein said housing includes a pair of housing portions connected together for relative movement, said opening being defined by a space between facing sides of said housing portions, and a pair of opposed sealing means respectively disposed in facing relation on said facing sides, said strip being movable between said sealing means, means for moving said housing portions apart to permit movement of said strip relative to said sealing means, said housing portions being movable toward each other to seal a portion of said strip with an aperture therein with said passageway.

13. The device of claim 10 further including a pair of resilient sealing members engaged respectively on opposed sides of said strip to seal the operatively positioned aperture in said passageway.

14. The device of claim 10 wherein said strip material is of plastic and has sprocket holes therein, and said feeding means includes sprocket wheel means cooperable with said sprocket holes for advancing said strip between said positions.

15. The device of claim 14 wherein said strip material is of a transparent film of ethylene glycol terpthalate.

* * * * *